(12) United States Patent
Paul et al.

(10) Patent No.: US 7,996,078 B2
(45) Date of Patent: Aug. 9, 2011

(54) SYSTEMS AND METHODS OF PHOTODYNAMIC-BASED CARDIAC ABLATION VIA THE ESOPHAGUS

(75) Inventors: Saurav Paul, Minnetonka, MN (US); Israel A. Byrd, Richfield, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 165 days.

(21) Appl. No.: 12/345,569

(22) Filed: Dec. 29, 2008

(65) Prior Publication Data
US 2009/0171331 A1    Jul. 2, 2009

Related U.S. Application Data

(63) Continuation-in-part of application No. 11/967,350, filed on Dec. 31, 2007.

(51) Int. Cl.
*A61N 1/30* (2006.01)
(52) U.S. Cl. .......................................... 604/21
(58) Field of Classification Search ............... 604/96.01, 604/97.01–97.03, 19–22; 606/192–194, 606/2–19
See application file for complete search history.

(56) References Cited

U.S. PATENT DOCUMENTS

| | | | | |
|---|---|---|---|---|
| 5,275,597 | A * | 1/1994 | Higgins et al. | 606/33 |
| 5,865,801 | A * | 2/1999 | Houser | 604/103.07 |
| 6,076,948 | A | 6/2000 | Bukosky et al. | |
| 6,579,285 | B2 | 6/2003 | Sinofsky et al. | |
| 6,749,623 | B1 * | 6/2004 | Hsi et al. | 607/88 |
| 6,811,562 | B1 | 11/2004 | Pless | |

OTHER PUBLICATIONS

Overholt, Bergein F. et al., "Photodynamic therapy for Barrett's Esophagus: Cardiac effects", Laser in Surgery and Medicine, 21:317-320 (1997).

* cited by examiner

*Primary Examiner* — Manuel A Mendez
(74) *Attorney, Agent, or Firm* — Trenner Law Firm, LLC

(57) ABSTRACT

Systems and methods for photodynamic ablation of cardiac tissue via an esophagus are disclosed. An exemplary system includes an ablation catheter having an expandable distal end for securing the ablation catheter in the esophagus. The distal end of the ablation catheter contains at least one light source operable to activate a photodynamic substance delivered to the target area of the cardiac tissue to be ablated and form a lesion. The system also includes at least one feedback device contained in the distal end of the ablation catheter. The at least one feedback device provides feedback for at least one of: positioning a distal end of an ablation catheter in a desired position in the esophagus adjacent a target area of the cardiac tissue to be ablated, forming an adequate lesion, and assessing lesion formation.

27 Claims, 6 Drawing Sheets

SYSTEMS AND METHODS OF PHOTODYNAMIC-BASED CARDIAC ABLATION VIA THE ESOPHAGUS

CROSS-REFERENCE TO RELATED APPLICATIONS

This application is a continuation-in-part of U.S. application Ser. No. 11/967,350 (filed 31 Dec. 2007), which is hereby incorporated by reference as though fully set forth herein.

BACKGROUND OF THE INVENTION a. Field of the Invention

This invention relates to systems and methods for ablation of cardiac tissue in a living being. In particular, the instant invention relates to systems and methods for ablation of cardiac tissue via the esophagus using photodynamic therapy.

b. Background Art

It is well known to use ablation catheters to create tissue necrosis in cardiac tissue to correct conditions such as atrial arrhythmia (including, but not limited to, ectopic atrial tachycardia, atrial fibrillation, and atrial flutter). Arrhythmia can create a variety of dangerous conditions including irregular heart rates, loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radiofrequency energy) to the heart tissue to create a lesion in the heart tissue. This lesion disrupts undesirable electrical pathways and thereby limits or prevents stray electrical signals that lead to arrhythmias.

Ablation catheters are typically placed near the cardiac tissue to be treated in one of two ways. Access to endocardial tissue is obtained by inserting the catheter within a vessel located near the surface of a patient's body (e.g., in an artery or vein in the leg, neck, or arm) and maneuvering the catheter through the circulatory system to the internal heart chambers. Access to epicardial tissue may be obtained by making a subxiphoid incision in the patient's body. Although the use of ablation catheters in this manner has resulted in less invasive treatment of arrhythmias, it would be desirable to develop a system and method for treatment of cardiac tissue that is even less invasive than current methods.

A need exists for systems and methods for ablation of cardiac tissue that will minimize and/or eliminate one or more of the above-identified deficiencies. A need also exists for providing feedback to the physician or other user of the systems and methods. Prior to lesion formation, for example, the physician or other user may desire to know that the ablation catheter is properly positioned adjacent the tissue to be ablated, that the ablation catheter can be maintained in the desired position during the ablation procedure, that the ablation catheter is not itself causing damage to the surrounding tissue. Following the lesion formation, for example, the physician or other user may desire to know that the ablation lesion has been successfully formed, in the desired position, and is the desired length, so that the procedure will not need to be repeated.

BRIEF SUMMARY OF THE INVENTION

It is desirable to provide a minimally invasive system and method for ablation of cardiac tissue in a living being, and to provide feedback to the physician or user to assist in the desired lesion formation. In particular, it is desirable to be able to ablate cardiac tissue while reducing surgical incisions or extensive maneuvering within the patient's circulatory system, and providing sufficient feedback to the physician or other user so that the ablation procedure is successful and does not need to be repeated.

An exemplary method for photodynamic ablation of cardiac tissue via an esophagus may include providing feedback for positioning a distal end of an ablation catheter in a desired position in the esophagus adjacent a target area of the cardiac tissue to be ablated. The method may also include securing the distal end of the ablation catheter in the esophagus in the desired position in the esophagus, and then actuating a light source in the ablation catheter to activate a photodynamic substance delivered to the target area of the cardiac tissue to be ablated.

An exemplary system for photodynamic ablation of cardiac tissue via an esophagus, may include an ablation catheter having an expandable distal end for securing the ablation catheter in the esophagus. The distal end containing at least one light source operable to activate a photodynamic substance delivered to the target area of the cardiac tissue to be ablated and form a lesion. The system may also include at least one feedback device contained in the distal end of the ablation catheter. The at least one feedback device provides visual, tactile, and/or other feedback for at least one of: positioning a distal end of an ablation catheter in a desired position in the esophagus adjacent a target area of the cardiac tissue to be ablated, forming an adequate lesion, and assessing lesion formation.

Another exemplary system for photodynamic ablation of cardiac tissue via an esophagus may include means for securing an ablation catheter in the esophagus. The system may also include means for providing feedback for positioning a distal end of the ablation catheter in a desired position in the esophagus adjacent a target area of the cardiac tissue to be ablated. The system may further include means for providing visual, tactile, and/or other feedback for forming an adequate lesion. Means may also be provided for activating a photodynamic substance from the ablation catheter and delivered to the target area of the cardiac tissue to be ablated to form a lesion, and means for providing feedback for assessing lesion formation.

The above-described system and method are advantageous because they provide a less invasive form of cardiac ablation as compared to current treatment methodologies and systems. The use of photodynamic therapy allows ablation of cardiac tissue via the esophagus thereby eliminating the need for surgical incisions and for maneuvering the ablation catheter through the circulatory system. As a result, the risk of complications for the patient is minimized and recovery time is reduced. The provision of feedback assists the physician or other user properly position and maintain the position of the ablation catheter prior to and during the ablation procedure so that an adequate lesion can be formed. The provision of feedback also assists the physician or other user to assess the quality of lesion formation.

The foregoing and other aspects, features, details, utilities and advantages of the present invention will be apparent from reading the following description and claims, and from reviewing the accompanying drawings.

DETAILED DESCRIPTION OF EMBODIMENTS OF THE INVENTION

Figure 3:
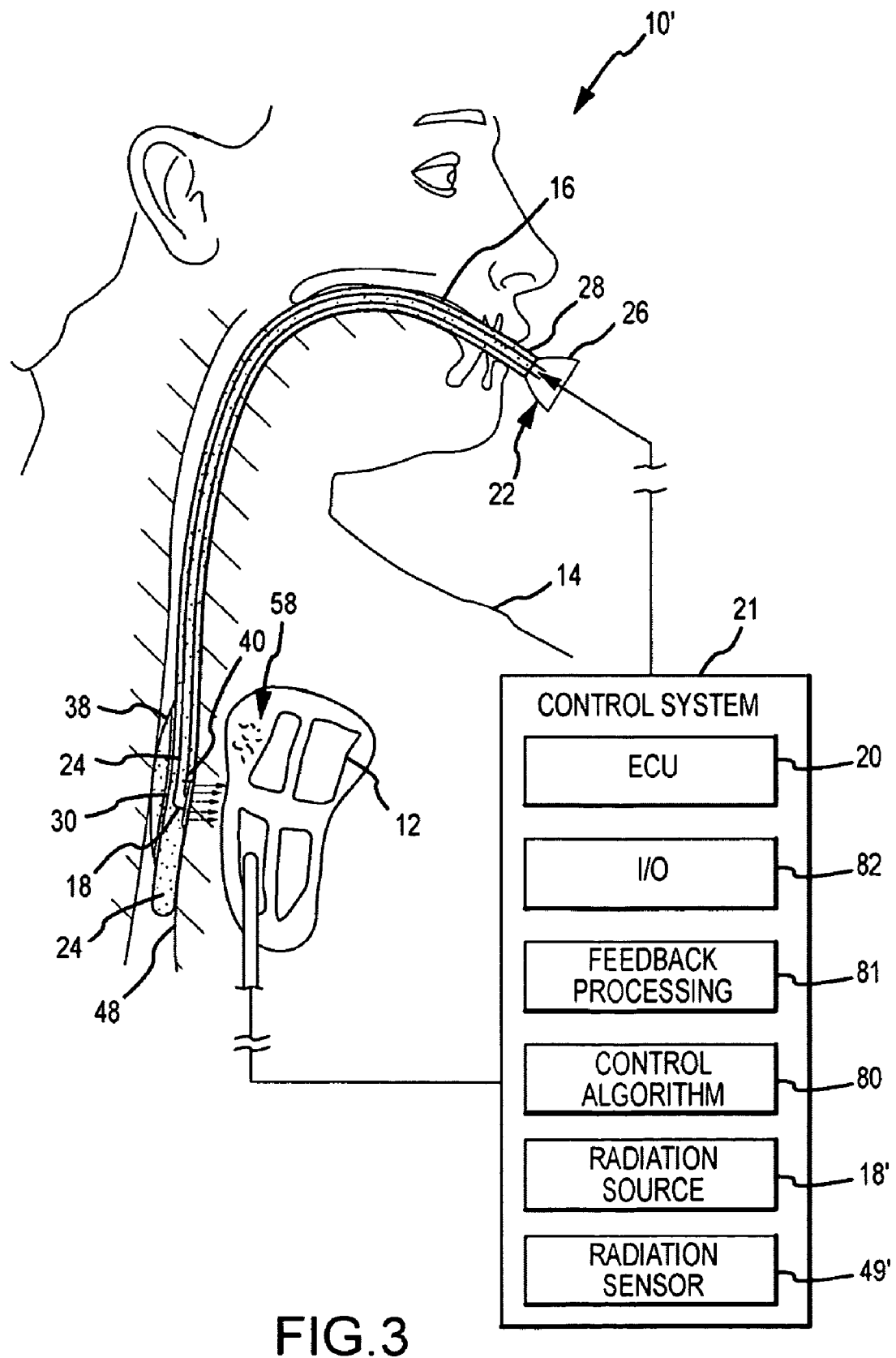
FIG. 3 is a diagrammatic view of a second system in accordance with the present teachings.
Figure 4:
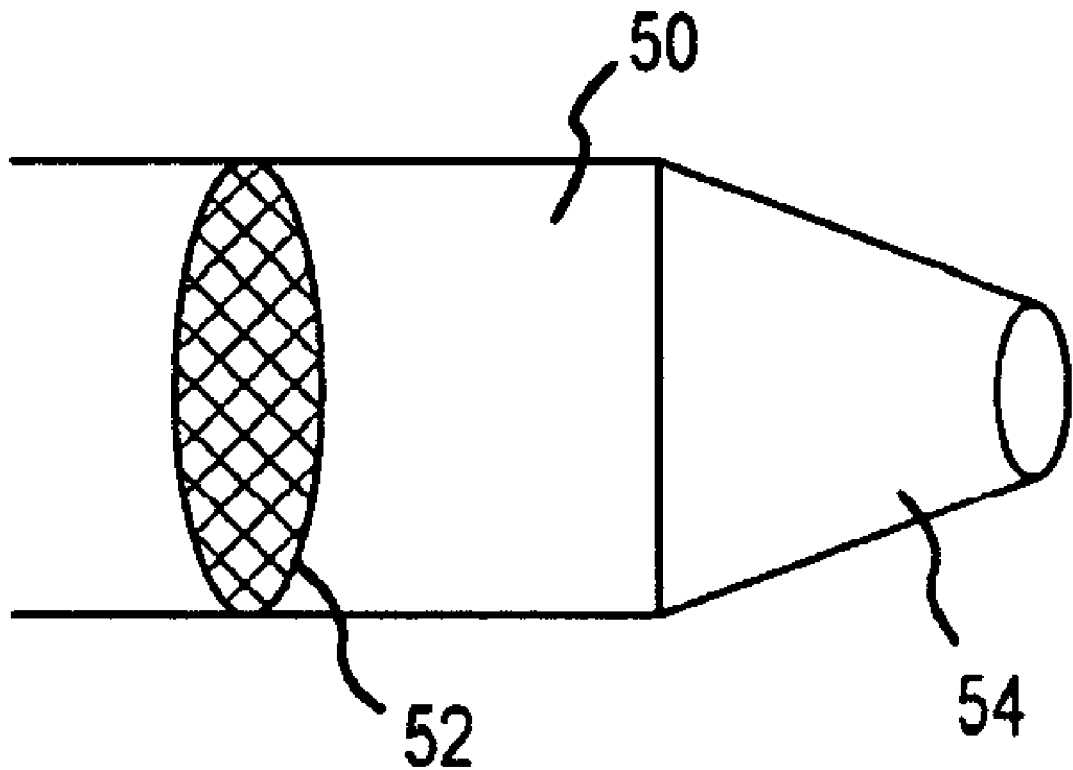
FIG. 4 is an enlarged diagrammatic view of one portion of the system of FIG. 3.
Figure 5:
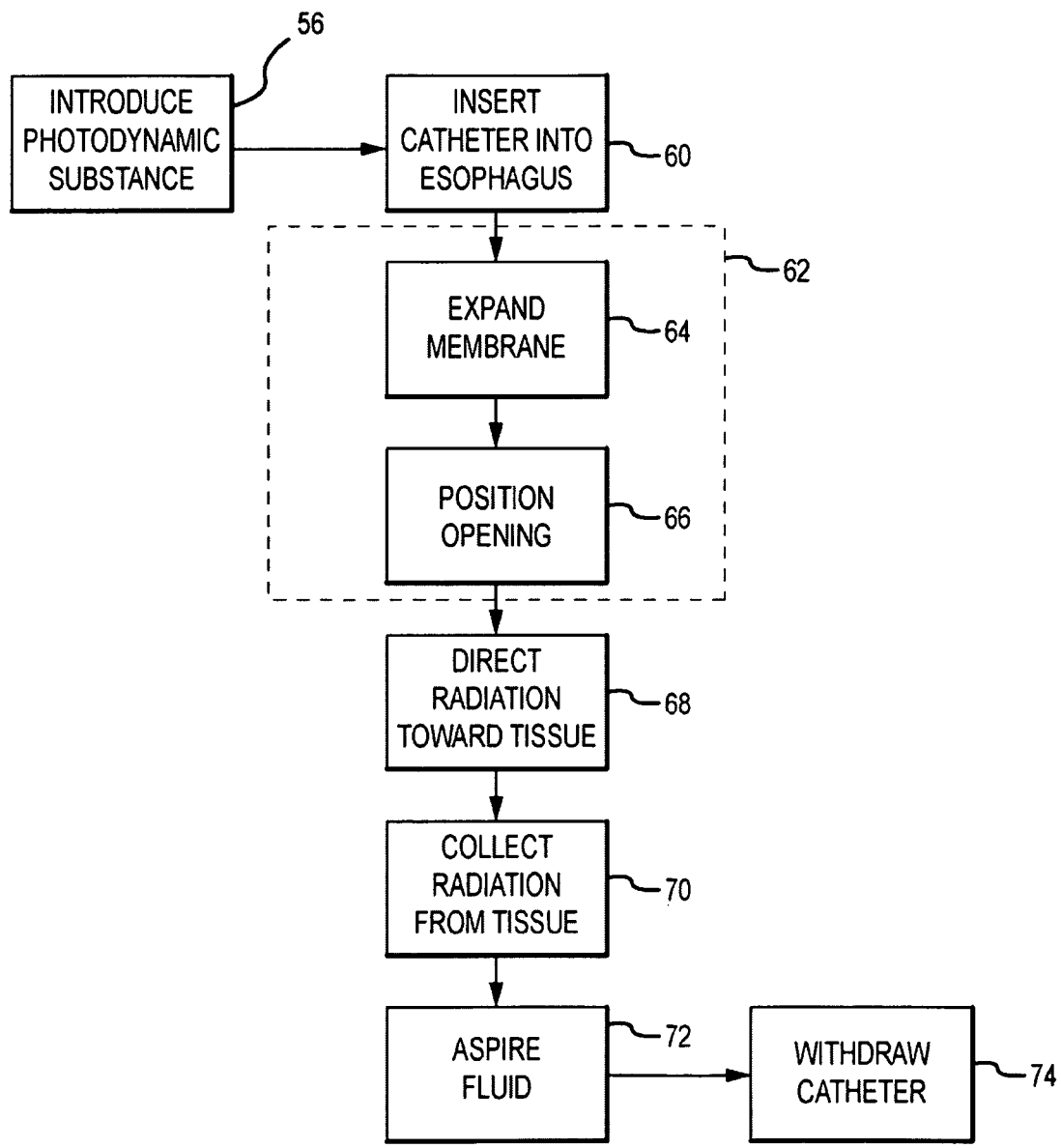
FIG. 5 is a flow chart diagram illustrating a method in accordance with the present teachings.

Referring now to the drawings wherein like reference numerals are used to identify identical components in the various views, FIGS. 1-4 illustrate exemplary embodiments of a system 10 for photodynamic ablation of cardiac tissue 12 in a patient's body 14 via the esophagus 36. The system 10 provides real-time feedback which may be implemented by a clinician and/or control algorithms during the ablation procedure. It is noted that other components typical of systems which are conventionally implemented for various medical procedures are not shown or described herein for purposes of brevity. Such components may nevertheless also be provided as part of, or for use with, the system 10. For example, the system 10 may be used in conjunction with an ECG recording system, and/or various control devices (e.g., a catheter handle) for performing the procedure. Such components are well understood in the medical devices arts and therefore further explanation is not necessary for a complete understanding of the invention. FIG. 5 illustrates exemplary embodiments of a method for photodynamic ablation of cardiac tissue 12 in a patient's body 14 via the esophagus 36. It is noted, however, that other embodiments, aspects, uses, and features will also be readily apparent to those having ordinary skill in the art after becoming familiar with the teachings herein.

In one embodiment, the tissue 12 comprises the atrial epicardium. It should be understood, however, that the system 10 may find application in connection with ablation of various cardiac tissues. In an exemplary embodiment, the system 10 may include a deformable, elongated body 16 (e.g., a guiding introducer), an electromagnetic radiation source 18, and a control system 21 including an electronic control unit (ECU) 20.

The elongated body 16 functions as an ablation catheter and is provided to house the radiation source 18 and associated electronics, including electrical signal conductors and possibly processing circuits (e.g., filtering, amplification, and other signal conditioning circuitry) and the feedback devices and associated circuitry discussed in more detail below. The elongated body 16 may also allow removal of bodily fluids or delivery of fluids and medicine into the patient's body 14. The elongated body 16 may further provide a means for transporting surgical tools or other instruments within the patient's body 14. The elongated body 16 may be formed from conventional materials such as polyurethane. The elongated body 16 is deformable and may be tubular. In an exemplary embodiment, the elongated body 16 may be guided within the body 14 by a guide wire or other means known in the art. The elongated body 16 has a proximal end 22 and a distal end 24. As used herein, the term "proximal" refers to a portion inserted adjacent the target tissue within the body of a patient and away from the physician or other user (referred to generally as a "clinician"). Also as used herein, the term "distal" refers to a portion directed toward the clinician (and opposite or away from the portion inserted within the body of a patient). The proximal end 22 may include an electrical connector 26 for connection to the control system 21 (e.g., the ECU 20). The elongated body 16 defines a lumen 28 extending between the proximal end 22 and the distal end 24. A port 30 and an opening 32 (shown in FIG. 2A) may be formed on substantially diametrically opposite points on a lateral wall 34 of the elongated body 16 for reasons described in more detail below. In accordance with the present teachings, the elongated body 16 is inserted into the patient's body 14 via the esophagus 36 and maneuvered within the esophagus 36 to a position near a region of interest in the tissue 12.

Figure 2A:
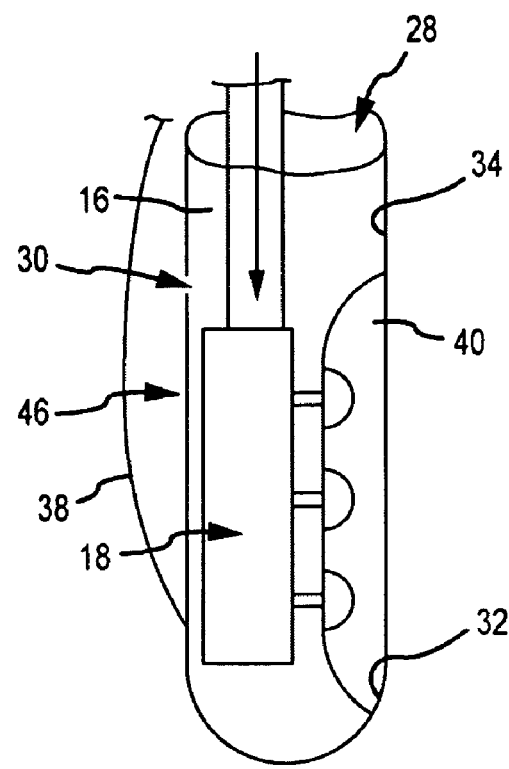
FIGS. 2A-C are enlarged plan views of one portion of the system of FIG. 1.
Figure 2B:
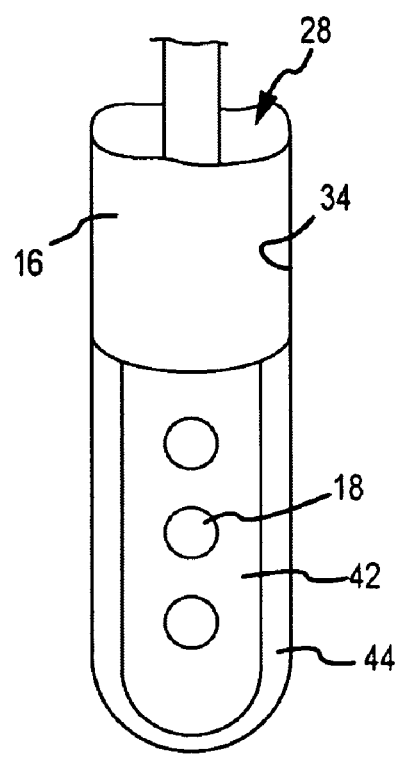
Figure 2C:
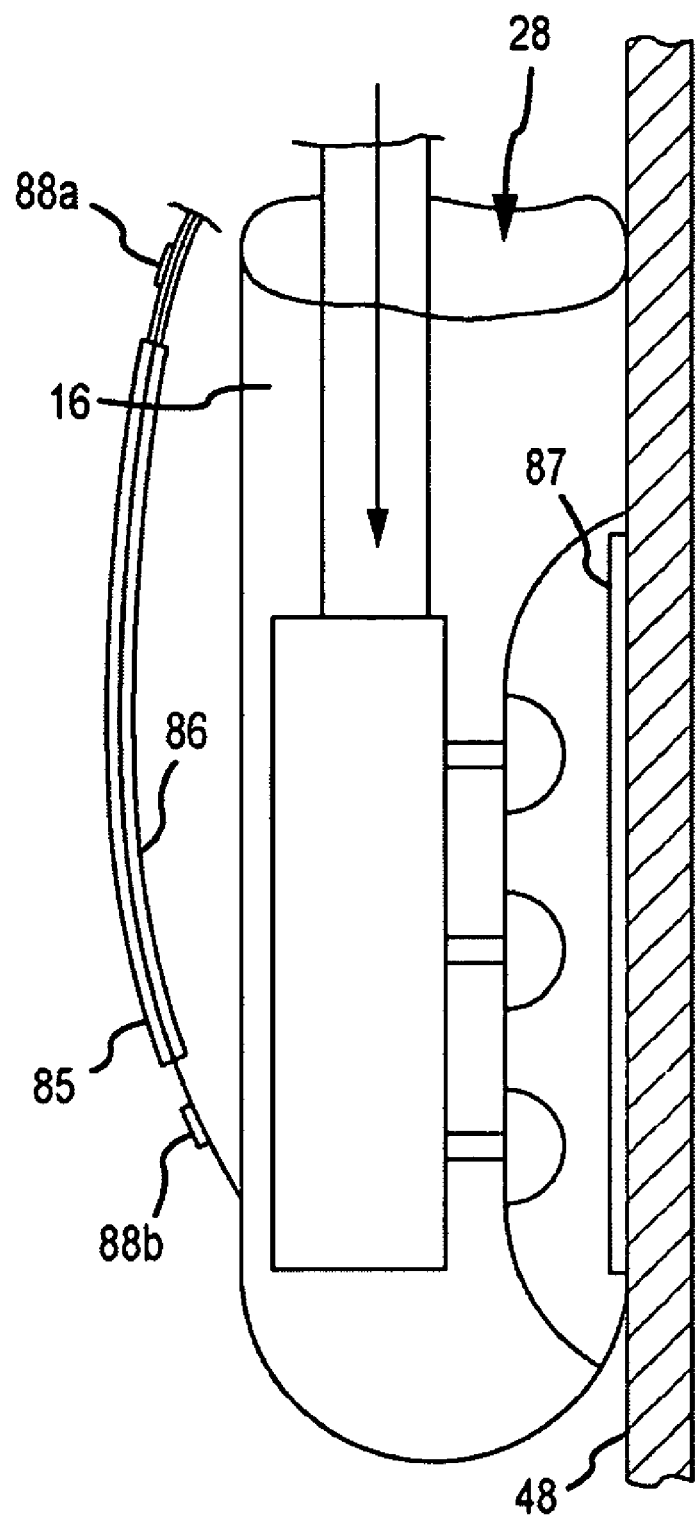

Referring to FIGS. 2A-C, in accordance with certain aspects of the present teachings, the distal end 24 of the elongated body 16 may include one or more structural features configured to position the distal end 24 within the esophagus 36 and to direct electromagnetic radiation from the radiation source 18. These features may include, for example, a deformable membrane 38, a lens 40, and reflective and opaque surfaces 42, 44.

The membrane 38 provides a means for positioning the distal end 24 of the elongated body 16 within the esophagus 36. The membrane 38 may be made from conventional materials including urethane (e.g., manufactured by Advanced Polymers Inc., 13 Industrial Way, Salem, N.H. 03079 USA). The membrane 38 is coupled to the elongated body 16 proximate the distal end 24 and covers the port 30 in the wall 34 of the elongated body 16. The membrane 38 is mounted to the elongated body 16 by using an adhesive such as ultraviolet (UV) adhesive. The membrane 38 defines an expandable space 46 between an interior surface of the membrane 38 and an exterior surface of the wall 34 of the elongated body 16. Fluid may be provided through the lumen 28 and/or the port 30 in the elongated body 16 and into the space 46 to deform the membrane 38 and inflate or expand the space 46 to secure the distal end 24 of the esophagus 36. The membrane 38 may be substantially diametrically opposite the opening 32. Upon deformation or inflation of the membrane 38, the distal end 24 of the elongated body 16 is urged to a position in which the distal end 24—and particularly the opening 32—are disposed against a wall 48 (see FIG. 1) of the esophagus 36.

The use of the membrane 38 provides several advantages. First, the membrane 38 places the distal end 24 of the elongated body 16 in a stable position and, therefore, provides a stable reference point that can be used by the ECU 20 in the evaluation and delivery of therapeutic ablation. Second, by placing the distal end 24 against the wall 48, the delivery of electromagnetic radiation is enhanced by reducing the distance of travel for the radiation and permitting stable directional focus of the electromagnetic energy toward the intended target. Although only one membrane 38 is shown in the illustrated embodiment, multiple membranes could be used. In particular, additional membranes could be mounted to the elongated body 16 and expanded or inflated using fluid through corresponding ports in the elongated body 16 to allow for more precise positioning and stability.

The fluid used for inflating and deflating the membrane 38 may comprise, for example, air (pneumatic fluid), water, contrast agent, or a radiopaque solution. Use of a contrast agent or radiopaque solution may be particularly useful when employed with fluoroscopy or other imaging procedures to assist the clinician in visualizing the location and movement of the elongated body 16 of the ablation catheter within the esophagus 36. Feedback from these procedures may be implemented to better position the distal end 24 of the elongated body 16 within the esophagus 36. The feedback may also be implemented during inflation of the membrane 38 to assist the clinician in gauging the extent of inflation of the membrane 38 so as to provide sufficient pressure to secure the distal end 24 of the elongated body 16 within the esophagus while reducing or altogether eliminating damage to the esophagus 36.

Sensing devices, such as pressure sensors 86 configured to read pressure of the fluid used for inflating the membrane 38, may also provide feedback which may be implemented to ensure proper inflation of the membrane 38. In an exemplary embodiment, feedback from pressure sensors 86 may be used to notify the clinician that the membrane 38 has been sufficiently inflated, or over-inflated. In another exemplary embodiment, feedback from pressure sensors may be implemented in a control algorithm 80 executed by the control unit 21 to automatically control the amount of fluid in the membrane 38 and thereby control proper inflation of the membrane 38. For example, the control unit 21 may use the feedback from the pressure sensors 86 to automatically inflate the membrane 38 to a predetermined pressure sufficient to secure the distal end 24 of the catheter within the esophagus 36, and to automatically deflate the membrane 38 if the pressure exceeds a threshold where the esophagus may become damaged.

Still other sensing devices may be implemented to provide tissue sensing data for contact assessment, e.g., between the distal end 24 of the catheter and the wall of the esophagus 36. Contact assessment feedback enables the clinician to maneuver and secure the distal end 24 of the catheter within the esophagus without bruising or puncturing the wall of the esophagus 36. In an exemplary embodiment, the sensing devices may include, by way of example, thermocouples 87, surface electrodes 88a-b, or piezoelectric sensors 85 mounted at the distal end 24 of the elongated body 16 of the catheter.

Thermocouples 87, surface electrodes 88a-b, and piezoelectric sensors 85 are well understood. Thermocouples 87 are a widely used type of temperature sensor which converts thermal potential into electric potential. This output may be correlated with tissue contact. Surface electrodes 88a-b discharge RF energy for sensing contact with tissue.

Piezoelectric sensors 85 typically include a piezoelectric material, such as a thin, flexible, polymer-based material. One such piezoelectric film is a polyvinylidene fluoride (PVDF) film (e.g., commercially available from the Sensor Products Division of Measurement Specialties, Inc., Norristown, Pa.). This PVDF film is approximately 28 µm thick, enabling the PVDF film to be readily housed within the catheter. In general, piezoelectric sensors generate a voltage in response to mechanical stress (e.g., flexure, pressure, and/or tension). Even minor deformation of some piezoelectric materials (e.g., on the order of nanometers) may generate a measurable voltage signal. These voltage signals may provide feedback corresponding to contact assessment.

The sensors are shown in FIG. 2C at various exemplary positions on the distal end 24 of the catheter. It is understood that these are shown merely for purposes of illustration. Specific numbers of sensors, types of sensors, and positioning of the sensors will depend on a wide variety of design considerations. Therefore, the sensors shown in FIG. 2C should not be construed as limiting in any manner.

Still other sensor devices may be implemented to provide tissue sensing data for contact assessment. Contact assessment feedback also enables the clinician to help ensure that there are no gaps between the distal end 24 of the ablation catheter and the wall of the esophagus 36 adjacent the target area of the cardiac tissue to be ablated. Determining contact with the tissue is often critical. Insufficient contact may result in a failure to form an adequate lesion. Proper contact with the esophagus adjacent the target area of the cardiac tissue helps ensure that the photodynamic substance is properly activated for adequate lesion formation.

Before continuing, it is noted that selection of sensors for use with the ablation catheter may be application-specific and depend at least in part on one or more design considerations, such as, but not limited to, the desired feedback, sensitivity and/or spatial constraints for housing the sensors in the catheter.

It is also noted that the feedback may include electrical signals generated by one or more of the various sensing devices provided in the elongated body 16 of the catheter. These electrical signals may be used to implement various control algorithms 80, e.g., for automatically inflating/deflating the membrane 38 or titrating the electromagnetic energy during an ablation procedure. The electrical signals may also be further characterized using a suitable processing 81. For example, the electrical signals may be converted to a corresponding contact condition and provided as output for the clinician via a suitable I/O device 82 (e.g., visual output on a computer monitor). Of course, the output is not limited to visual output. For example, a contact condition may be output to the user as an audio signal or tactile feedback (e.g., vibrations) on the handle of the catheter. In any event, circuitry for conveying feedback to the clinician and/or implementing the feedback automatically in a control algorithm may be readily provided by those having ordinary skill in the electronics arts after becoming familiar with the teachings herein.

Having properly positioned and secured the distal end 24 of the elongated body 16 within the esophagus 36, the system may be implemented to form the lesion on the target area of the cardiac tissue. Accordingly, the lens 40 is provided to allow transmission of radiation from the radiation source 18 while protecting the source 18 and the other electronic components from potential damage due to, for example, contact with bodily fluids. The lens 40 may be made from glass, such as crown glass; or conventional plastics, such as polycarbonate, polymethyl methacrylate (PMMA or acrylic), and allyl diglycol carbonate (sold under the registered trademark "CR-39" by PPG Industries, Pittsburg, Pa. 15272 USA); or a gel, such as hydrogel or silicone hydrogel; or photoresist materials such as SU-8. The lens 40 covers the opening 32 in the wall 34 of the elongated body 16. The lens 40 extends about only a portion of the circumference of the elongated body 16 and may have an elliptical curve to focus the electromagnetic radiation.

The surfaces 42, 44 are provided to control emission of electromagnetic radiation from the distal end 24 of the elongated body 16. The surface 42 reflects radiation emitted by the source 18 in a direction opposite the wall 48 of the esophagus 36 back towards the wall 48 to increase therapeutic efficiency. The surface 42 is reflective and may comprise a mirror which may be attached to the radially inner side of the lens 40 using an adhesive. The lens 40 and the surface 42 may be deformable such that the curvature and focal length of the lens 40 and/or of the surface 42 can be manipulated by flexing the elongated body 16 and/or adjusting the fluid pressure in the space 46 within the membrane 38 (in a manner analogous to the lens in the human eye, which alters its shape, and consequently its focal length, in response to changes in zonular tension induced by ciliary muscle contraction). The surface 44 is opaque and inhibits passage of electromagnetic radiation emitted by the source 18 in directions away from the wall 48 of the esophagus 36. The surface 44 may extend about a portion of the circumference of the elongated body 16 on either side of the lens 40. The surface 44 may comprise an absorptive coating on the radially inner surface of the wall 34. The surface 44 may extend around about half (180°) of the circumferential surface of the wall and may be centered behind the reflective surface 42.

Referring again to FIG. 1, the electromagnetic radiation source 18 is provided to generate a set of electromagnetic radiation for delivery to the tissue 12. The source 18 may comprise, for example, a light emitting diode (LED) or laser (e.g., a laser diode). The source 18 may produce a monochromatic or spectral radiation, and the radiation may be polarized or unpolarized. The source 18 may generate radiation at various points along the electromagnetic spectrum including, for example, visible light, infrared, near infrared, ultraviolet, and near ultraviolet radiation. The radiation source 18 may emit radiation in a controlled manner responsive to signals received from the control unit 20.

Figure 1:
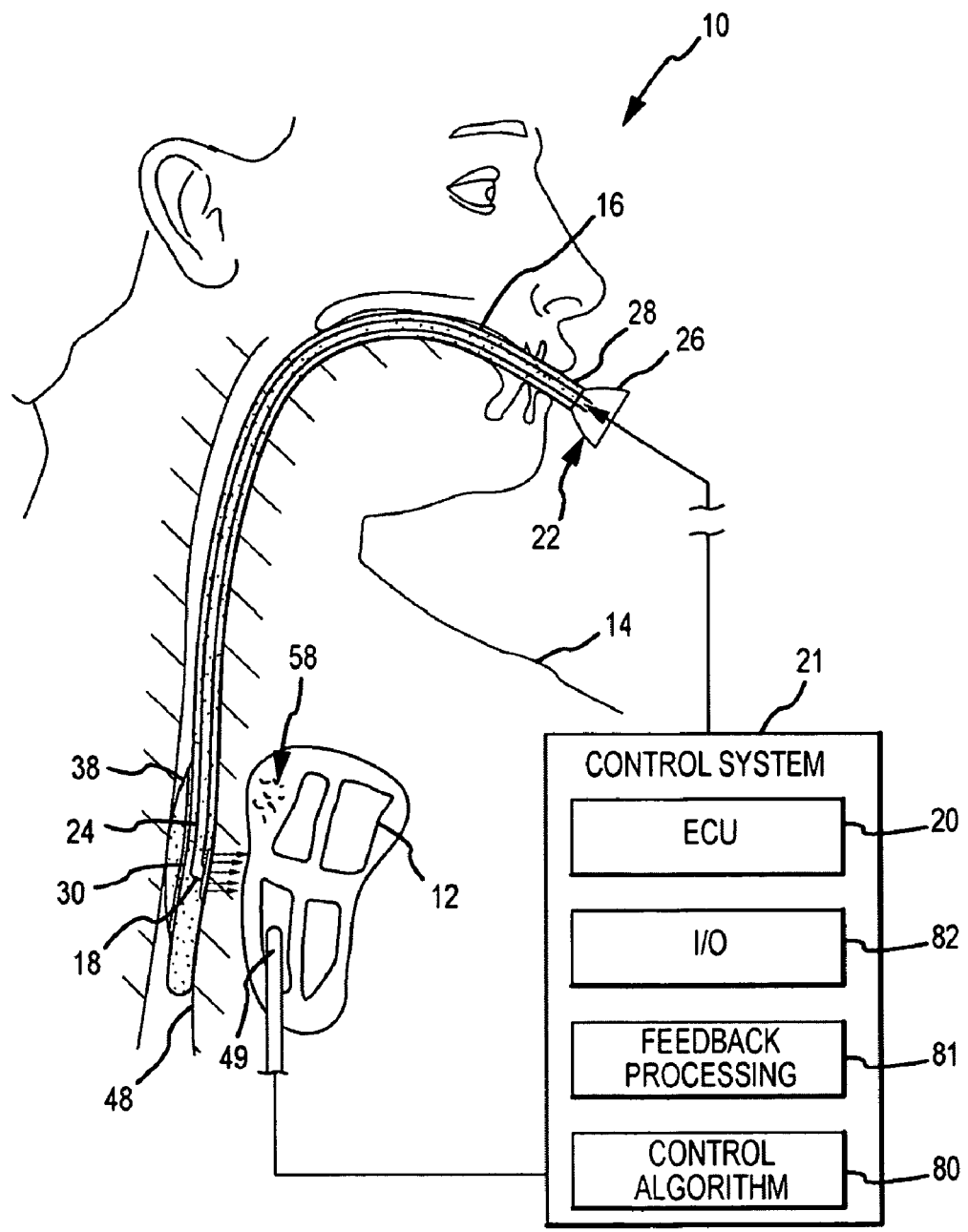
FIG. 1 is diagrammatic view of a first system in accordance with the present teachings.

The system 10 may also include an electromagnetic radiation sensor 49. The sensor 49 is provided to generate a signal in response to electromagnetic radiation originating from the tissue 12 in response to radiation transmitted by the source 18. This signal may be used by the ECU 20 to measure the radiation incident on the tissue 12 in order to provide feedback to assist positioning the source 18, to titrate radiation levels to affect therapy, and to assess tissue necrosis (lesion creation). The radiation originating from the tissue 12 may comprise a portion of the radiation emitted from the source 18 or may comprise radiation reflected or emitted by a photodynamic substance in the tissue 12 as described in greater detail below. The sensor 49 may comprise a photodiode. As shown in FIG. 1, the sensor 49 may be supported at the distal end of another elongated, deformable body (e.g., a catheter) and, in accordance with one aspect of the present teachings, may be positioned on the opposite side of the tissue 12 that is being treated relative to the distal end 24 of elongated body 16. For example, the sensor 49 may be positioned within a heart chamber on the endocardial side of the tissue 12 and may receive radiation originating from the tissue 12 in response to radiation emitted from the source 18 on the epicardial side of the tissue 12. Alternatively, the sensor 49 may be located within the elongated body 16 at the distal end 24 of the elongated body 16 proximate the source 18.

The electronic control unit ("ECU") 20 of the control system 21 provides a means for selectively activating the source 18 to direct a set of electromagnetic radiation to the tissue 12. The ECU 20 may utilize its own processor such as an application specific integrated circuit (ASIC), or a separate programmable microprocessor or microcontroller, e.g., that of the control system 21. The control system 21 may include a central processing unit (CPU) and an input/output (I/O) interface 82 through which the ECU 20 may receive a plurality of input signals including signals generated by various feedback sensors on or remote from the elongated body 16 and generate a plurality of output signals to convey information regarding the operation of the radiation source 18 and the effects of treatment. These output signals may convey information through variation in amplitude of frequency of voltage or current and may, for example, be used to generate images relating to the tissue 12 on a conventional display monitor (not shown). The input and output signals may comprise electrical signals. Alternatively, signals may be transmitted wirelessly in a conventional manner.

In the embodiment shown in FIGS. 1, 2A and 2B, the radiation source 18 is disposed at the distal end 24 of the elongated body 16 and the radiation sensor 49 is likewise disposed at the distal end of another body. Referring now to FIG. 3, in another embodiment of the system 10' a radiation source 18' is disposed proximate the proximal end 22 of the elongated body 16 while a radiation sensor 49' may likewise be disposed proximate the proximal end of another body. Radiation from the radiation source 18' is transmitted to the distal end 24 through one or more optic fibers 50. Similarly, radiation may be collected at the distal end of the other body and provided to the sensor 49' through one or more fibers 50. The fibers 50 are conventional and may be made from various glass compositions (e.g., silica) or plastics (e.g., polymethyl methacrylate (PMMA) surrounded by fluorinated polymers). The fibers 50 include a core and a cladding with the core having a higher refractive index than the cladding. The fibers 50 may further include a buffer layer and a jacket as is known in the art. The fibers 50 may, for example, comprise any of a variety of common fibers (e.g., sold by Polymicro Technologies, Inc., Edmund Optics, Inc., or Keyence Corporation). The fibers 50 are disposed within the elongated body 16 and may extend from the proximal end 22 to the distal end 24 of the elongated body 16 where they terminate at the lens 40. Again, although the sensor 49' is illustrated as disposed at the end of a separate elongated body, the sensor 49' could alternatively be located at the proximal end 22 of the elongated body 16, and radiation could be received through the same fiber in the elongated body 16 through which radiation is transmitted or another fiber within the elongated body 16.

The amount of radiation needed to activate the photodynamic substance may vary depending on a variety of different factors. For example, the amount of radiation needed may be higher if the concentration of photodynamic substance in the heart tissue is lower, and vice versa.

In an exemplary embodiment, the concentration of photodynamic substance may be determined by mixing a marker (e.g., biodegradable magnetic particles) with the photodynamic substance prior to injection into the patient's body. A sensing device may be provided in the distal end 24 of the catheter and configured to read the marker, and correlate the marker readings to a concentration of the photodynamic substance. For example, where the marker includes magnetic particles, the sensing device may be configured to read the magnetic field at the target area of the cardiac tissue. This reading may be provided as feedback for determining the concentration of the photodynamic substance.

Likewise, the amount of radiation needed may need to be adjusted based on the desired depth of the lesion and/or one or more quality of the target tissue. In any event, the radiation transmitted by the fiber 50 may be controlled or amplified using different components. Referring to FIG. 4, a filter 52 may be disposed within the fiber 50 or may cover the proximal or distal end of the fiber 50 to control the passage of radiation by permitting passage of radiation of a selected wavelength (or range of wavelengths) while filtering out optical noise. A lens 54 may also be used to focus the radiation exiting the fiber 50. The lens 54 may be located at the distal end of the fiber 50. Alternatively, the lens 40 may be shaped to focus the transmission of radiation.

In addition, one or more sensors may also be implemented to provide feedback for assessing lesion formation. In an exemplary embodiment, the sensors include thermocouples. As discussed above, thermocouples may be implemented to determine a thermal gradient of the target area of the cardiac tissue. The temperature readings may be correlated to lesion formation. In yet another exemplary embodiment, a marker may be provided at the target area of the cardiac tissue prior to lesion formation, and then movement of the marker may be monitored following lesion formation to assess the quality of the lesion. For example, where the marker is a radiopaque substance, movement of the radiopaque substance would be greater prior to lesion formation. Formation of a quality lesion would effectively halt or significantly limit movement of the radiopaque substance. Thus, this monitoring of movement of the radiopaque substance before and after lesion formation may be provided as feedback for assessing the quality of the lesion that was formed.

Referring now to FIG. 5, a method for ablation of cardiac tissue 12 in accordance with the present teachings will be described. The method may begin with the step 56 of introducing a photodynamic substance 58 (see FIG. 1) to the tissue 12. The substance 58 is relatively inert until activated by radiation of a specific wavelength. Upon activation, the substance 58 induces tissue necrosis through a variety of methods such as apoptosis. The substance 58 may comprise a photosensitive chemical or drug or other substance. For example, the substance 58 may comprise 5-aminolevulinic acid (ALA), meso-tetra-hydroxyphenyl-clilorin (mTHPC); an electrochromic and potentiometric dye such as di-2-ANEPEQ, di4-ANEPPS, or di-8-ANEPPS; neuromodulators such as Acetylcholine; a cardioplegic solution; or a cryocardioplegic solution (e.g., hypothermic saline). The substance 58 may comprise the substance (porfimer sodium) sold by Axcan Pharma Inc. under the registered trademark "PHOTOFRIN" or the substance sold by Scotia Holdings plc under the registered trademark "FOSCAN." Alternatively, the substance 58 may be a radiopaque substance such as the substance sold by Amersham Health AS under the registered trademark "HYPAQUE" or any of a variety of conventional radiopaque dyes. The substance 58 may also comprise a substance that modifies electrical conductivity in the tissue 12 such as saline, one of the above-identified photosensitizes, or an anti-stenotic agent. The substance 58 may also comprise a cytotoxic chemical.

The substance 58 may be introduced into the tissue 12 in a variety of ways such that the substance 58 is absorbed into the cells in the tissue 12 or binds with the cell membranes. For example, the substance 58 may be introduced through in-situ delivery, arterial delivery and/or systemic delivery. One method of in-situ delivery may be through electroporation in which a site limited electric shock is used to create an electric field to cause expansion of the cells in the tissue 12 for a period of time to allow the substance 58 to enter the cells. Alternative methods of in-situ delivery may be by application of an electrical field on the substance 58 itself or using acoustic waves (e.g. ultrasound) to break through the tissue boundary. Alternatively, the substance 58 may be infused through the artery, such as the coronary artery, to allow perfusion into the tissue 12. It should be understood that these methods of introducing the substance 58 to the tissue 12 are exemplary only and not intended to limit the scope of the invention.

It should be understood that the system and method according to the present teachings may also involve use of multiple photodynamic substances 58. For example, diagnosis or treatment may occur in a region of interest having multiple tissue types. Because different tissues react differently to the substances 58 (e.g., some tissues are more responsive than others), it may be advantageous to use different substances within the same region of interest.

The method according to the present teachings may further include the step 60 of inserting the elongated body 16 into the esophagus 36. The elongated body 16 may be inserted by the physician in a conventional manner through the mouth or nose and into the esophagus 36. During step 60, feedback may be provided by one or more techniques described in more detail above in order to assist the clinician in positioning the elongated body 16 of the catheter in the esophagus.

The method may further include the step 62 of locating the distal end 24 of the elongated body 16 proximate the tissue 12. Feedback may be provided by one or more techniques described in more detail above in order to assist the clinician in locating the elongated body 16 of the catheter proximate the tissue 12. For example, tissue sensing data may be provided. The physician may maneuver the elongated body 16 using a guide wire or in other conventional manners through the esophagus 36 to a position at which treatment can be provided to the tissue 12. In accordance with one aspect of the present teachings, step 62 may include the substep 64 of expanding the space 46 between the exterior surface of the elongated body 16 and the interior surface of the membrane 38. As discussed hereinabove, this step may include the substep of providing fluid to the space 46 through the lumen 28 and the port 30 in the wall 34 of the elongated body 16. The expansion of the membrane 38 and the space 46 urges the distal end 24 into engagement with the esophageal wall 48 for positional stability and a reduction in scattering and transmission distance for the electromagnetic radiation generated by the radiation source 18. Feedback may be provided by one or more techniques described in more detail above in order to assist the clinician, or in automatically inflating/deflating the membrane 38. After expansion of the membrane 38 and the space 46, step 62 may further include the substep 66 of positioning the opening 32 relative to the tissue 12.

The method may continue with the step 68 of directing electromagnetic radiation from the distal end 24 of the elongated body 16 towards the tissue 12. As discussed above, the electromagnetic radiation activates the substance 58 in the tissue 12 leading to tissue necrosis. Also as discussed above, the radiation may be generated from a source 18 located at the distal end 24 of the elongated body 16 or from a source 18' located remote from the distal end 24 of the elongated body 16. Feedback may be provided by one or more techniques described in more detail above in order to determine and/or adjust the amount of radiation needed for an adequate lesion. The method may further include the step 70 of collecting electromagnetic radiation originating from the tissue 12 in response to the radiation emitted from the distal end 24 of the elongated body 16. As discussed above, radiation may be collected on an opposite side of the tissue 12 relative to the distal end 24 of the elongated body 16 (e.g., within a heart chamber on the endocardial side of the tissue 12) and provided directly to the sensor 49 located at the distal end of another elongated body or indirectly to the sensor 49' located at the proximal end of the elongated body via one or more fibers 50. Radiation may alternatively be collected at the distal end 24 of the elongated body 16 by sensors 49, 49' located at the distal or proximal ends 24, 22 of the elongated body 16. The distal end 24 of the elongated body 16 and the opening 32 may be realigned and step 68 may be repeated to the extent necessary for proper treatment. Feedback may be provided by one or more techniques described in more detail above in order to assist the clinician in determining whether an adequate lesion was formed.

Once ablation of the tissue 12 is complete, the method may continue with the step 72 of aspirating fluid from the space 46 and the lumen 28 to deflate the membrane 38. The method may conclude the step 74 of withdrawing the elongated body 16 from the esophagus 36.

A system and method in accordance with the present teachings offers one or more of a number of advantages. For example, the system and method provide a less invasive form of cardiac ablation as compared to various current treatment methodologies and systems. The use of photodynamic therapy allows ablation of cardiac tissue via the esophagus thereby eliminating the need for surgical incisions or for maneuvering an ablation catheter through the circulatory system. As a result, both the risk of complications for the patient and the recovery time are reduced.

Although several embodiments of this invention have been described above with a certain degree of particularity, those skilled in the art could make numerous alterations to the disclose embodiments without departing from the scope of this invention. For example, although the illustrated embodiments shows a single radiation source 18 or 18' and a single optic fiber 50 used in connection with source 18', multiple radiation sources could be employed to enable radiation to be transmitted using different radiation characteristics (e.g., frequency, intensity, phase angle, polarization) for use in generating a variety of therapeutic effects. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A system for photodynamic ablation of cardiac tissue via an esophagus, comprising:
    an ablation catheter having an expandable distal end for securing the ablation catheter in the esophagus, the distal end containing at least one light source operable to activate a photodynamic substance delivered to the target area of the cardiac tissue to be ablated and form a lesion;
    at least one feedback device contained in the distal end of the ablation catheter, the at least one feedback device providing feedback for at least one of: positioning a distal end of an ablation catheter in a desired position in the esophagus adjacent a target area of the cardiac tissue to be ablated, assessing tissue contact, forming an adequate lesion, and assessing lesion formation.

2. The system of claim 1, wherein the feedback for positioning the ablation catheter in the esophagus includes tissue sensing data.

3. The system of claim 2, wherein the tissue sensing data includes output from surface electrodes at the distal end of the ablation catheter.

4. The system of claim 2, wherein the tissue sensing data includes output from piezoelectric sensors at the distal end of the ablation catheter.

5. The system of claim 2, wherein the tissue sensing data includes pressure data from a fluid used to expand the distal end of the ablation catheter.

6. The system of claim 1, further comprising a control unit configured to automatically expand the distal end of the ablation catheter to secure the ablation catheter in the esophagus.

7. The system of claim 6, wherein the control unit is further configured to automatically stop expanding the distal end of the ablation catheter when the distal end of the ablation catheter is sufficiently secured in the esophagus.

8. The system of claim 1, wherein the feedback for forming an adequate lesion includes concentration of the photodynamic substance sensed at the distal end of the ablation catheter.

9. The system of claim 8, wherein the concentration of the photodynamic substance corresponds to magnetic markers sensed at the distal end of the ablation catheter.

10. The system of claim 1, wherein the feedback for assessing lesion formation is from thermocouples on the distal end of the ablation catheter.

11. The system of claim 1, wherein the feedback for assessing lesion formation is from movement of radiopaque markers sensed at the distal end of the ablation catheter.

12. A system for photodynamic ablation of cardiac tissue via an esophagus, comprising:
    means for securing an ablation catheter in the esophagus;
    means for providing feedback for positioning a distal end of the ablation catheter in a desired position in the esophagus adjacent a target area of the cardiac tissue to be ablated;
    means for providing feedback for forming an adequate lesion means for activating a photodynamic substance from the ablation catheter and delivered to the target area of the cardiac tissue to be ablated to form a lesion; and
    means for providing feedback for assessing lesion formation.

13. The system of claim 12, further comprising:
    means for automatically expanding the distal end of the ablation catheter to secure the ablation catheter in the esophagus; and
    means for automatically stopping the expanding based on the feedback for positioning to reduce or eliminate damage to the esophagus.

14. A method for photodynamic ablation of cardiac tissue via an esophagus, comprising:
    providing feedback for positioning a distal end of an ablation catheter in a desired position in the esophagus adjacent a target area of the cardiac tissue to be ablated; and
    securing with an expandable distal end of the ablation catheter the distal end of the ablation catheter in the esophagus in the desired position in the esophagus, and then actuating a light source in the ablation catheter to activate a photodynamic substance delivered to the target area of the cardiac tissue to be ablated.

15. The method of claim 14, wherein the feedback for positioning the ablation catheter in the esophagus includes tissue sensing data.

16. The method of claim 15, wherein the tissue sensing data includes output from surface electrodes at the distal end of the ablation catheter.

17. The method of claim 15, wherein the tissue sensing data includes output from piezoelectric sensors at the distal end of the ablation catheter.

18. The method of claim 15, wherein the tissue sensing data includes pressure data from a fluid used to expand the distal end of the ablation catheter.

19. The method of claim 14, further comprising:
    automatically expanding the distal end of the ablation catheter to secure the ablation catheter in the esophagus, and automatically stopping the expanding based on the feedback for positioning to reduce or eliminate damage to the esophagus.

20. The method of claim 14, further comprising providing feedback for forming an adequate lesion.

21. The method of claim 20, wherein the feedback for forming an adequate lesion includes concentration of the photodynamic substance sensed at the distal end of the ablation catheter.

22. The method of claim 21, wherein the concentration of the photodynamic substance corresponds to markers sensed at the distal end of the ablation catheter.

23. The method of claim 22, wherein the markers are magnetic particles.

24. The method of claim 14, further comprising providing feedback for assessing lesion formation.

25. The method of claim 24, wherein the feedback for assessing lesion formation is from thermocouples on the distal end of the ablation catheter.

26. The method of claim 24, wherein the feedback for assessing lesion formation is from movement of markers sensed at the distal end of the ablation catheter.

27. The method of claim 26, wherein the markers are radiopaque particles.

* * * * *